United States Patent [19]

Teller et al.

[11] Patent Number: 5,082,816
[45] Date of Patent: Jan. 21, 1992

[54] LEAD-ZIRCONATE CATALYSTS

[75] Inventors: Raymond G. Teller, Aurora; James F. Brazdil, Jr., Mayfield Village; Joseph P. Bartek, Highland Heights; Ann M. Brussee, Wickliffe, all of Ohio

[73] Assignee: The Standard Oil Company, Cleveland, Ohio

[21] Appl. No.: 555,812

[22] Filed: Jul. 23, 1990

Related U.S. Application Data

[60] Continuation of Ser. No. 437,306, Nov. 17, 1989, abandoned, which is a continuation of Ser. No. 293,002, Jan. 3, 1989, abandoned, which is a division of Ser. No. 901,106, Aug. 28, 1986, Pat. No. 4,795,848.

[51] Int. Cl.$^5$ .............. B01J 21/16; B01J 21/12; B01J 21/06; C10G 25/02
[52] U.S. Cl. .................. 502/84; 423/593; 502/178; 502/239; 502/242; 502/304; 502/340; 502/343; 502/349; 502/350; 502/351
[58] Field of Search ............ 502/84, 178, 239, 242, 502/340, 343, 344, 345, 349, 350, 304, 351; 423/593

[56] References Cited

U.S. PATENT DOCUMENTS

| | | | |
|---|---|---|---|
| 3,141,902 | 7/1964 | Huntley et al. | 502/349 |
| 3,184,415 | 5/1965 | Huntley et al. | 502/349 |
| 4,497,971 | 2/1985 | Eastman et al. | 585/561 |
| 4,636,248 | 1/1987 | Ogata et al. | 423/593 |
| 4,636,378 | 1/1987 | Pastor et al. | 502/525 |
| 4,696,810 | 9/1987 | Shirasaki et al. | 423/593 |
| 4,795,848 | 1/1989 | Teller et al. | 585/500 |

Primary Examiner—Paul E. Konopka

[57] ABSTRACT

Catalysts comprising lead doped zirconium compounds are particularly effective in an oxidative process for upgrading low molecular weight alkanes to higher molecular weight hydrocarbons, and especially for upgrading methane to form ethane and ethylene. The catalysts can be employed in a process performed at elevated temperatures and in the presence or absence of gaseous oxygen. The catalysts are substantially free of PbO and uncombined Pb and remain stable for long periods of time.

21 Claims, 1 Drawing Sheet

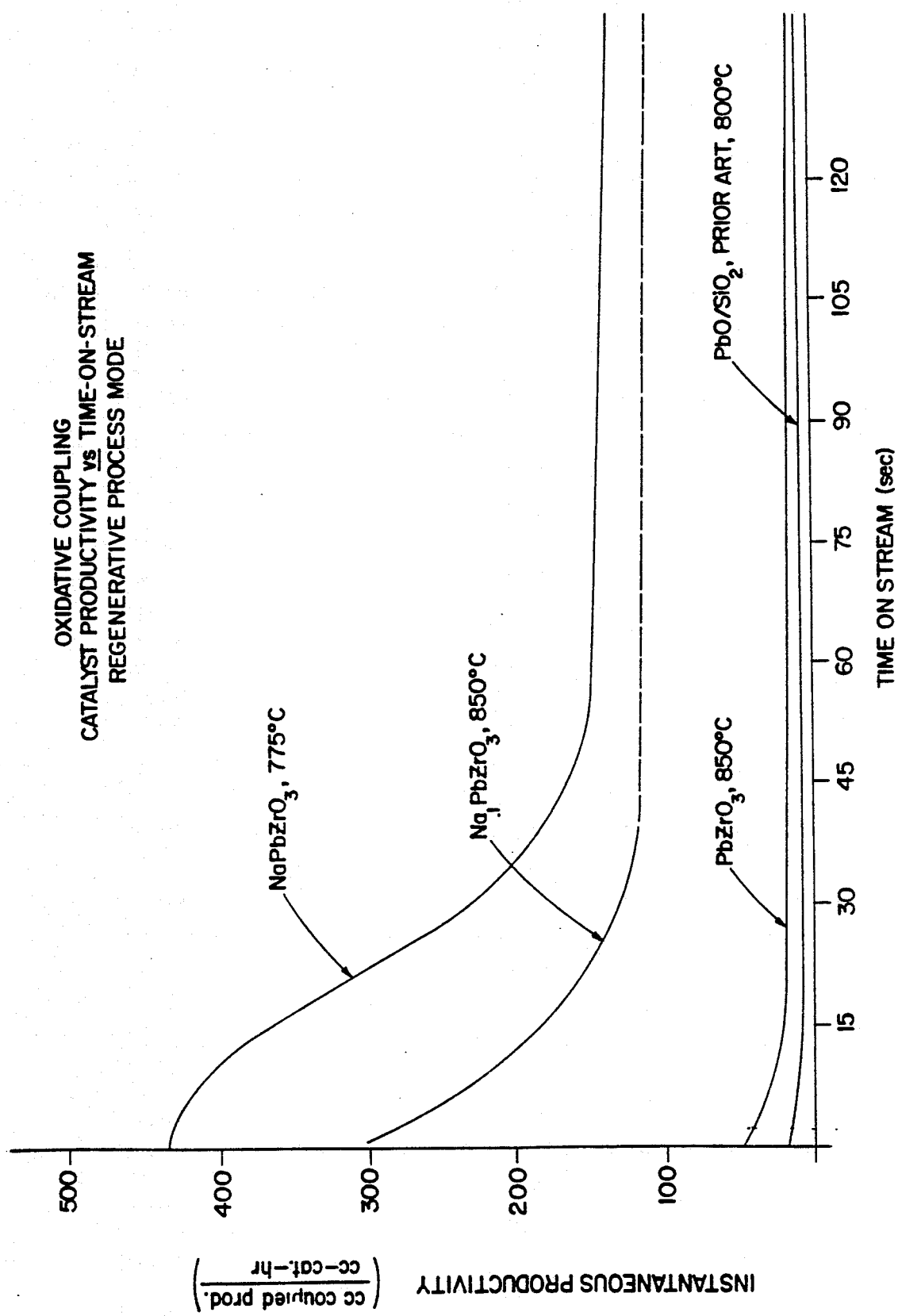

LEAD-ZIRCONATE CATALYSTS

This application is a continuation of application Ser. No. 437,306, field Nov. 17, 1989, now abandoned, which is a continuation of Ser. No. 293,002, filed Jan. 3, 1989, now abandoned, which is a division of Ser. No. 901,106, filed Aug. 28, 1986, now U.S. Pat. No. 4,795,848.

FIELD OF THE INVENTION

This invention relates to upgrading low molecular weight alkanes to form higher order hydrocarbons. More specifically, the present invention is directed to a vapor phase reaction of low molecular weight alkanes in the presence of lead zirconate catalyst formulations to synthesize higher molecular weight hydrocarbons, especially the reaction of methane to synthesize ethane and ethylene. The higher order hydrocarbons can be reacted to form predominantly liquid hydrocarbon products.

BACKGROUND OF THE INVENTION

The predominant source of methane, an abundant low molecular weight alkane, is natural gas, which is found in porous reservoirs generally associated with crude oil reserves. From this source comes most of the natural gas used for heating purposes. Quantities of natural gas are also known to be present in coal deposits and are by-products of crude oil refinery processes and bacterial decomposition of organic matter. Natural gas obtained from these sources is generally utilized as a fuel at the site.

Prior to commercial use, natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons, which comprise ethane and heavier hydrocarbons. Natural gas can be treated at the wellhead or at a central processing station. The processed natural gas comprises predominantly methane, and minor quantities of ethane, propane, butane, pentane, carbon dioxide and nitrogen. Generally, processed natural gas comprises from about 50 volume percent to more than 95 volume percent methane.

Natural gas is used principally as a source of heat in residential, commercial and industrial service. Methane also has commercial uses in the chemical processing industry. The largest use for methane, other than as a primary fuel, is in the production of ammonia and methanol. Ammonia is a basic ingredient of fertilizers and is also a common feedstock in the production of petrochemicals, such as acrylonitrile and nylon-6. Methanol is a precursor material for products, such as formaldehyde, acetic acid and polyesters.

Methane has also been used as a feedstock for the production of acetylene by electric-arc or partial-oxidation processes. Another commercial use for methane is in the production of halogenated products, such as methyl chloride, methylene chloride, chloroform and carbon tetrachloride. Methane also reacts with ammonia to produce hydrogen cyanide.

Most processed natural gas is distributed primarily through an extensive pipeline distribution network. As gas reserves in close proximity to gas usage decrease, new sources in distant locations require additional transportation. Distant sources may not be amenable to transport by pipeline, such as sources that are located in areas requiring economically unfeasible pipeline networks or in areas requiring transport across large bodies of water. This concern has been addressed in several ways.

One solution has been to build a production facility at the site of the natural gas deposit to manufacture one specific product. This approach is limited because the natural gas can be used only for one product, preempting other feasible uses for methane, Another approach has been to liquify methane and transport the liquid methane in specially designed tanker ships Natural gas can be reduced to 1/600th of the volume occupied in the gaseous state by cryogenic processing, and with proper procedures, safely stored or transported. The processes for liquifying natural gas to a temperature of about $-162°$ C., transporting, and revaporizing are complex and energy intensive.

Still another approach has been to convert methane to higher order hydrocarbon products that can be easily handled and transported, preferably hydrocarbon products that exist in a liquid state. The conversion of methane to higher order hydrocarbons, especially ethane and ethylene, would retain the versatility of the material for use as a precursor in chemical processing. Known dehydrogenation and polymerization processes are available for further conversion of ethane and ethylene to liquid hydrocarbons, such as the processes taught by Chu in U.S. Pat. No. 4,120,910 and Chen et al in U.S. Pat. No. 4,100,218, both disclosures being incorporated herein by reference. In these ways, easily transportable commodities may be derived directly from natural gas at the wellhead. The drawback to implementing such a process, however, has been in obtaining a sufficient conversion rate of methane to higher order hydrocarbons.

Catalytic coupling of alkanes is known in the art. While it is possible to convert alkanes to higher order hydrocarbons, major undesirable by-products are CO and $CO_2$.

The catalytic oxidative coupling of methane at atmospheric pressure and at temperatures of from about 500° to 1,000° C. has been investigated by several researchers. G. E. Keller and M. M. Bhasin reported the synthesis of ethylene via oxidative coupling of methane over a wide variety of metal oxides supported on an alpha-alumina structure, *Journal of Catalysis* 73, 9–19 (1982). This article discloses the use of single component oxide catalysts that exhibited methane conversion to higher order hydrocarbons at rates no greater than 4 percent. The process by which Keller and Bhasin oxidized methane was cyclic, varying the feed composition between methane, nitrogen and air (oxygen) to obtain higher selectivities.

West German Patent DE 32 37 079.2 to Baerns and Hinsen reports the use of supported, single component oxide catalysts. The process taught by Baerns and Hinsen utilizes low oxygen partial pressure to give a high selectivity for the formation of ethane and ethylene. The conversion of methane to such desired products, however, remains low, on the order of from about four to about seven percent conversion.

U.S. Pat. Nos. 4,443,644–4,443,649 inclusive to Jones et al teach methods for synthesizing hydrocarbons from methane by contacting methane with a single component metal oxide at temperatures between about 500° and 1,000° C. The processes taught in these patents produce high selectivities to higher order hydrocarbons but at very low conversion rates, on the order of less than 4 percent overall conversion to higher order hydrocarbons. PbO is used as the single component metal oxide in United States Patent 4,443,647.

U.S. Pat. No. 4,495,374 discloses the use of an alkaline earth metal or a component thereof with a reducible metal oxide to improve the conversion of methane to higher hydrocarbons. United States Patent 4,499,322 discloses the use of an alkali metal or a compound thereof as a promoter to improve methane conversion. In each case conversion is carried out at a temperature in the range of about 500° to 1000° C.

Through experimentation with different types of catalysts under various reaction conditions, it was discovered that catalyst activity can be increased by carrying out methane coupling reactions at relatively high temperatures, that is, temperatures above about 900° C. The formation of hydrocarbons is favored at the higher temperatures, while smaller amounts of CO and $CO_2$ are formed as undesired by-products.

These results suggest that high yields of higher order hydrocarbons could be obtained if an alkane was upgraded in the presence of a PbO-containing catalyst at a high temperature, such as about 900° to 950° C. However, PbO (litharge) melts and volatilizes at a temperature of about 888° C. Lead melts at an even lower temperature of 327° C. Volatilization leads to a loss of catalyst from the reactor and a resulting decrease in reactor productivity. More importantly, release of Pb and PbO from the reactor into the environment cannot be tolerated. For these reasons, reaction temperatures above about 850° C. can only be employed for reaction times that are sufficiently short to avoid volatilization of PbO. Such short reaction times are unsuitable in a commercial operation.

It has been suggested that a PbO-containing catalyst may be employed in a commercial alkane coupling process at a temperature somewhat below the volatilization temperature of the PbO, such as about 800° to 850° C., but the use of lead oxide even at these temperatures is somewhat limited. The alkane coupling reaction is an exothermic reaction accompanied by the release of large quantities of heat. It is very difficult to control the temperature throughout the reactor within a narrow temperature range. For this reason it is not unusual for the reactor to have a temperature profile that includes high temperature zones or hot spots at or above 888° C. The PbO can thus volatilize in these zones. This problem exists whether the lead oxide catalyst is supported or unsupported. Thus, the use of the known PbO-containing catalysts in high temperature, commercial alkane coupling processes is limited.

There exists a need in the art for a catalyst suitable for upgrading alkanes to higher order hydrocarbons at high reaction temperatures. The catalyst should exhibit high temperature stability and high activity in converting alkanes to higher order hydrocarbons, including liquid hydrocarbon products. The catalyst should retain its chemical activity, structural integrity and mechanical properties at temperatures up to about 1550° C. In addition, volatilization of Pb and PbO from the catalyst should be negligible at temperatures up to about 1550° C. The catalyst should have long catalyst life and should be suitable for use in natural gas conversion to higher order hydrocarbon products at high selectivities and at commercially feasible methane conversion rates. There also exists a need in the art for a process to upgrade methane to produce predominantly ethane and ethylene.

SUMMARY OF THE INVENTION

This invention aids in fulfilling these needs in the art by providing a process for the conversion of low molecular weight alkanes to higher order hydrocarbons. The process comprises contacting a low molecular weight alkane at a reaction temperature of from about 500° C. to about 1500° C with a catalyst of the formula $$Pb\ Zr_z\ A_a\ B_b\ O_x$$

wherein
  A is Mg, Ca, Sr, Ba, Zn, Ce, Sc, Y, Ti, Hf or mixtures thereof;
  B is Li, Na, K, Rb, Cs or mixtures thereof; and wherein
  z is about 1 to about 100;
  a is 0.0 to about 100;
  b is 0.0 to about 100;
  x is the number of oxygens needed to fulfill the valence requirements of the other elements; and
  wherein the catalyst is substantially free of PbO and uncombined Pb.

This invention also provides a process for upgrading low molecular weight alkanes to substantially liquid hydrocarbon products in which the process comprises
  a) contacting a low molecular weight alkane at a reaction temperature of from about 500° to about 1500° C. in the presence of a catalyst of the formula $$Pb\ Zr_z\ A_a\ B_b\ O_x$$

wherein
  A is Mg, Ca, Sr, Ba, Zn, Ce, Sc, Y, Ti, Hf or mixtures thereof;
  B is Li, Na, K, Rb, Cs or mixtures thereof; and wherein
  z is about 1 to about 100;
  a is 0.0 to about 100;
  b is 0.0 to about 100;
  x is the number of oxygens needed to fulfill the valence requirements of the other elements so as to synthesize a higher order hydrocarbon product effluent; and
  wherein the catalyst is substantially free of PbO and uncombined Pb; and
  b) dehydrogenating the higher order hydrocarbon product effluent, and/or contacting the effluent with a catalyst to yield a substantially liquid hydrocarbon product.

In addition, this invention provides a novel catalyst for the conversion of a low molecular weight alkane to a higher order hydrocarbon. The catalyst comprises a composition having the formula $$Pb\ Zr_z\ A_a\ B_b\ O_x$$

wherein
  A is Mg, Ca, Sr, Ba, Zn, Ce, Sc, Y, Ti, Hf or mixtures thereof;
  B is Li, Na, K, Rb, Cs or mixtures thereof; and wherein
  z is about 1 to about 100;
  a is 0.0 to about 100;
  b is 0.0 to about 100;
  x is the number of oxygens needed to fulfill the valence requirements of the other elements; and
  wherein (a+b) is about 0.1 to about 100 and the catalyst is substantially free of PbO and uncombined Pb.

This invention is especially useful for upgrading methane to predominantly ethane and ethylene and to the subsequent conversion of the ethane and ethylene to liquid hydrocarbon products. The invention provides a number of advantages over previously disclosed processes for the conversion of low molecular weight alkanes, including higher selectivities to higher order hydrocarbons, higher conversion rates, higher productivities and longer catalyst life. The catalyst maintains its activity and the ability to produce coupled hydrocarbon products with time-on-stream, while activity to form carbon oxides is reduced. Volatilization of Pb and PbO from the catalyst is negligible at temperatures up to about 1550° C.

BRIEF DESCRIPTION OF THE DRAWING

The advantages provided by this invention will be more fully appreciated by reference to the following description and to the Figure, which is a graph showing instantaneous productivity as a function of time for the oxidative coupling of methane carried out according to the present invention. Instantaneous productivity obtained with a prior art process using a supported PbO catalyst is included in the Figure for purposes of comparison.

DETAILED DESCRIPTION OF THE INVENTION

In the process of the present invention at least one low molecular weight alkane in the vapor phase is contacted with a solid oxidative catalyst to form a higher order hydrocarbon, which can be further processed if necessary to yield a substantially liquid hydrocarbon product. The oxidative catalyst of the invention comprises a novel multicomponent formulation.

As used herein, the phrase "low molecular weight alkane" refers to at least one alkane of the formula $C_N H_{2N+2}$, where N is an integer of 1 to 5. Thus, the phrase low molecular weight alkane includes methane, ethane, propane, butane and pentane, each a major or minor constituent found in natural gas.

The expression "higher order hydrocarbon" as used herein refers to the product of a reaction wherein an alkane is reacted to yield at least one hydrocarbon having at least one carbon atom more than that found in the reactant alkane.

The phrase "substantially liquid hydrocarbon product" as used herein, refers to at least one hydrocarbon that exists primarily in the liquid state at about 25° C. and about one atmosphere.

The process of this invention can be carried out with a known lead zirconate composition identified in the literature as $PbZrO_3$. This composition is described by Jona et al in *Physical Review*, 105, 3, 849–856 (1957). A $PbZrO_3$ composition was prepared for use in the present invention and was found to be substantially free of PbO and uncombined Pb Characterization of the composition by elemental analysis and X-ray diffraction crystallography was consistent with the analytical data published by Jona et al.

It has been found that the activity of the lead zirconate composition as a catalyst and the life of the catalyst can be improved by incorporating a promoter in the catalyst. It has also been found that the promoter increases the selectivity of the catalyst for higher order hydrocarbons. The catalyst of the invention is a lead doped zirconium compound containing such a promoter. The catalyst is a solid and comprises a composition described by the empirical formula $$Pb\ Zr_z\ A_a\ B_b\ O_x$$

wherein

A is Mg, Ca, Sr, Ba, Zn, Ce, Sc, Y, Ti, Hf or mixtures thereof;

B is Li, Na, K, Rb, Cs or mixtures thereof; and wherein z is about 1 to about 100;

a is 0.0 to about 100;

0.0 to about 100; and x is the number of oxygens needed to fulfill the valence requirements of the other elements; and wherein (a+b) is about 0.1 to about 100 and the catalyst is substantially free of PbO and uncombined Pb.

The catalyst employed in the process of the invention can exist in a chemically oxidized state, chemically reduced state or partially oxidized or reduced state. In any event, the catalyst is substantially free of PbO and uncombined Pb at temperatures between about 20° C. and about 1570° C. in all of its chemical states. Upon reduction, the lead zirconate is substantially free of Pb or PbO.

The catalyst of the invention is a solid state matrix comprised of $PbZrO_x$. Components A and B in the catalyst of the invention are employed as promoters. Component A is preferably Mg, Ca, Y, Ti or mixtures thereof. Most preferably component A is Mg, Ca or mixtures thereof. Component B is preferably Na.

While the amount of component A and component B expressed as the quantity (a+b) is about 0.1 to about 100, it will be understood that the quantity (a+b) should not be so large that a reduction in catalytic activity results. In addition, component A and component B should not be present in amounts that would result in the formation of Pb or PbO that could melt or volatilize when the catalyst is in use. These difficulties can generally be avoided if the quantity (a+b) does not exceed the value of z. Generally, the quantity (a+b) is about 0.1 to about 3, preferably about 0.1 to about 2. In the particularly preferred catalyst of the invention the value of a is 0, the value of b is from about 0.5 to about 1, and the value of z is about 1 to about 15.

The catalyst can be unsupported or it can be supported on any suitable carrier. For example, a catalyst support could be employed to dilute or bind the active components in the catalyst. Alumina, silica, alumina-silica, magnesium aluminate, calcium aluminate, silicon carbide, clay and the like, are typical of suitable catalyst supports. The catalyst can be disposed on a support by known methods, such as impregnation to incipient wetness and coprecipitation techniques.

In addition, the catalyst of the invention can be employed as a support or as a co-catalyst for another alkane coupling catalyst. Because of the thermal stability and very high melting point of the catalyst of the invention, the operating temperature range of other alkane coupling catalysts can be raised when the catalyst of the invention is utilized as a support or co-catalyst. The catalyst of the invention is particularly well-suited for these purposes when the alkane coupling catalyst is soluble in $PbZrO_3$. Lead, Sn, Sb, Bi, Ge, In and Mn are typical examples of alkane coupling catalysts that can be combined with the catalyst of the invention.

The catalyst can be prepared by conventional means, such as by mixing compounds containing the catalyst components in a liquid solution or slurry and heating the resulting composition. The catalyst precursor can be recovered from the liquid, and then dried and calcined.

A preferred catalyst preparation method involves impregnation of a sol of zirconium oxide (zirconia) with a solution of a salt of a PbO-containing compound, such as a nitrate or acetate. When a promoter is included in the catalyst, component A and component B can be included in the solution with the Pb compound. The resulting mixture can be dried and calcined.

It is preferred that the catalyst be heat treated prior to being used for the conversion of low molecular weight alkanes to higher order hydrocarbons, although this is not required. Heat treating has been found to increase catalyst stability. The catalyst is preferably heat treated at a temperature of about 800° C. to about 1200° C. Pretreatment can be carried out after startup of the reactor, but prior to the introduction of the reactant species into the reactor.

The catalyst can be formed into solid particles of various shapes and sizes as required to adapt the catalyst to the type of reactor employed. The active components can be coated on a support core, dispersed in a support matrix or be self-supported. Particle size, porosity and shape should be controlled to ensure good mass transport of reactants to active sites on the catalyst.

A reaction gas mixture containing a low molecular weight alkane is fed to a reactor containing the catalyst. One low molecular weight alkane of special interest is methane. Methane, in the form of natural gas, can have associated with it minor amounts of other hydrocarbons, such as ethane, propane, butane and pentane. The alkane can also be mixed with water, carbon dioxide, nitrogen, carbon monoxide and inert gases. The presence of gas phase additives does not adversely affect the efficiency of the present process. Indeed, the process of the invention is effective for upgrading not only methane, but also the other low molecular weight alkanes found in natural gas. Although reference herein may be directed to upgrading methane, it is understood that the same remarks are applicable for other low molecular weight alkanes.

The process of the present invention is an oxidative reaction. The reaction can be carried out in the substantial absence of gaseous oxygen, oxygen for the reaction being derived almost entirely from the oxygen in the multicomponent catalyst employed in the reaction. Alternatively, an oxidizer, such as an oxygen-containing gas, can be employed in the reaction Typical oxidizing gases are $O_2$, $N_2O$, $CO$, $CO_2$ and $H_2O$. Gaseous oxygen can be provided as substantially pure oxygen or diluted with nitrogen, carbon dioxide, or other inert gases. Oxygen can also be provided in air.

A reaction feed stream comprises from about 15 volume percent to about 100 volume percent methane and from zero volume percent to about 50 volume percent oxygen. When oxygen is cofed with a low molecular weight alkane to a reactor containing the catalyst, the reaction feed stream comprises about 1 to about 35 volume percent oxygen, preferably about 15 to about 25 volume percent oxygen.

A diluent gas, such as an inert gas, can be present in the reaction feed stream. The diluent gas increases the selectivity of the coupling reaction. If necessary, the diluent gas can be separated from the product stream from the reactor using conventional techniques. Nitrogen, argon and helium are typical diluent gases that can be employed.

The process of the present invention is carried out by contacting the gaseous reactants, predominantly methane and oxygen, with the solid lead zirconate catalyst in a suitable reactor, such as a fluid bed reactor, fixed bed reactor, moving bed reactor, membrane reactor or swing reactor system, i.e., a reactor for a process cycling between a reaction step and a catalyst re-oxidation step. The density of the catalyst of the invention can be readily controlled with catalyst support materials to adapt the catalyst to a fluidized bed reactor. The reaction can be conducted in a continuous mode or in a batch mode.

The process of the invention can be carried out over a broad range of reaction temperatures. Relatively high reaction temperatures can be employed because the catalyst is thermally stable. Since the catalyst is substantially free of PbO, there is virtually no risk that PbO will be volatilized even though the reaction is conducted at temperatures higher than those deemed practical in prior processes. In addition, it has been found that the reaction can be carried out at lower reaction temperatures, such as the temperatures currently employed in methane coupling reactions with PbO-containing catalysts. Thus, the need to control the temperature of the reactor to avoid high temperature zones in which the catalyst would decompose is less critical in the present invention because the catalyst is useful over a broad temperature range.

The process of this invention makes it possible to carry out catalytic oxidative coupling under conditions in which thermal pyrolysis of reactants and products can occur. These conditions include high temperatures and short residence times in the reactor. The heat required for endothermic pyrolysis reactions is at least partially supplied by the exothermic oxidative coupling reaction. As a result, methane can be directly converted to higher molecular weight hydrocarbons enriched in olefins, $C_{3+}$ saturates and $C_{5+}$ liquid hydrocarbons.

The reaction temperature will typically be maintained at about 500° C. to about 1500° C., and preferably about 750° C to about 1000° C. The process of the invention can be carried out at a temperature of about 900° to about 1500° C., which is above the temperature at which PbO volatilizes. A reaction temperature of about 1100° C. to about 1500° C. is preferred for higher temperature operation. The existence of high temperature zones in the reactor or hot spots within these temperature ranges will not adversely affect catalyst performance or have an adverse impact on the environment, which could occur with a lead oxide catalyst.

The process of this invention can be carried out over a wide range of operating pressures. While process equipment costs are lower for lower reactor pressures, higher pressures may favor alkane coupling reactions. The pressure will typically be about 1 to about 10 atm, preferably about 1 to about 3 atm. The optimum pressure for a particular installation can be determined with a minimum of experimentation.

The lead zirconate catalyst employed in the process of this invention exhibits high catalytic activity. In addition, the catalyst has good mechanical properties, such as resistance to abrasion and compression. For these reasons it is possible to pass the gaseous reactants through the reactor at high reactant flow rates.

The contact time of the reactants with the catalyst should be sufficient to maximize conversion of the low molecular weight alkanes to higher order hydrocarbons. Sufficient contact time can be obtained by passing gaseous reactants through the reactor at a gas hourly space velocity (GHSV) of about 100 $hr^{-1}$ to about 10,000 $hr^{-1}$. In the preferred embodiment of this invention, the reactants are passed through the reactor at a GHSV of about 800 hr$^{-1}$ to about 8,000 hr$^{-1}$, since this will give higher productivities than lower flow rates under otherwise similar conditions. The particularly preferred GHSV of the reactants is about 4,000 hr$^{-1}$ to about 8,000 hr$^{-1}$.

The use of gas phase promoters in alkane coupling reactions carried out in a regenerative (cyclic) process mode is known in the art. Chlorine-containing compounds have been found to be suitable for this purpose. An advantage of the process and catalyst of the invention is that the catalyst does not form stable chlorine compounds that would adversely affect catalyst activity and catalyst life. Other conventional gas phase promoters can also be employed in practicing the process.

When methane is upgraded according to the invention, ethane, ethylene and higher molecular weight hydrocarbons are produced. In addition, by-product water, carbon monoxide and carbon dioxide are obtained. An advantage of this invention is that the lead zirconate catalysts are not known to form stable carbonates with $CO_2$ in the product stream, which could adversely affect catalyst life and reactor productivity.

The conversion of methane by the process of the invention is as high as about 10 percent to about 25 percent while maintaining reaction selectivity for the formation of higher order hydrocarbons in the range of from about 50 percent to about 85 percent. This process upgrades methane to produce an effective yield of higher order hydrocarbons of from about 5 percent to about 18 percent, significantly higher yields than those obtained with some other processes and catalysts.

When natural gas comprises a portion of the feed stream, the minor amounts of other low molecular weight alkanes are upgraded in a manner similar to that of methane. For instance, ethane can be converted to butane and propane. It is envisioned that unconverted alkanes can be recycled to the reaction to increase the overall yield of products. If the reaction contemplates recycling unreacted natural gas, then the portion of the feed stream containing minor amounts of the alkanes ethane, butane, propane and pentane may change, depending on the efficiency of the product recovery apparatus. These alkanes need not be fully removed from the reactor feed stream. The resultant products are substantially higher order hydrocarbons.

In order to demonstrate the superior performance of the process of this invention, several embodiments of the invention using a lead zirconate catalyst for the oxidative coupling of methane were compared with a prior art process using a PbO catalyst on $SiO_2$ support. Each process was carried out in a regenerative process mode, that is, oxygen was not cofed with the gaseous reactants. Process performance was evaluated based upon the rate of production of coupled products per hour and the quantity of catalyst in the reactor. The results are expressed as instantaneous productivity", which is defined as follows:

$$\text{Instantaneous Productivity} = \frac{\text{cc of coupled products produced}}{\text{hr}} \times \frac{1}{\text{cc of catalyst in the reactor}}$$

The unit of measure is the reciprocal of time, typically expressed as hr$^{-1}$.

Another useful measure is the "relative total productivity," which is defined as the instantaneous productivity multiplied by the time on stream. This amounts to an integration of the area under each of the curves in the Figure and is a measure of total catalyst productivity.

For comparison purposes, a catalyst containing PbO on $SiO_2$ was used in the oxidative coupling of methane at 800° C. The process was similar to that described in Example 4 of U.S. Pat. No. 4,443,647. Instantaneous productivity for this process is plotted in the Figure, and the relative total productivity for the process was found to be 12 hr$^{-1}$.

The process was repeated, except that a lead zirconate catalyst identified as $PbZrO_3$ was used according to the invention. Because the lead zirconate catalyst was substantially free of PbO and uncombined Pb, it was possible to carry out the process at a higher temperature, namely 850° C. Instantaneous productivity is plotted in the Figure. For the overall process, relative total productivity was found to be 26 hr$^{-1}$. Instantaneous productivity for the process of the invention was more than two times the relative total productivity of the prior art process using PbO/$SiO_2$ as catalyst.

Another process according to the invention was carried out with a lead zirconate catalyst containing a small amount of Na as a promoter. The catalyst had the approximate formula $Na_{0.1}PbZrO_3$. This process was also carried out at 850° C. Instantaneous productivity is plotted in the Figure. The solid line was obtained by fitting a curve to the experimental data actually obtained, and the broken line was obtained by extrapolating the actual results based upon experience obtained with other catalysts in the same reactor. The relative which is 5 times higher than that obtained with the lead zirconate catalyst without a promoter. In comparison with the relative total productivity of 12 hr$^{-1}$ obtained with the prior art process in which a supported PbO catalyst was used, the relative total productivity was more than an order of magnitude greater using a novel catalyst of the invention.

Another catalyst of the invention was prepared and the coupling process was repeated. In this case, the catalyst had the approximate formula $NaPbZrO_3$, and the coupling reaction was carried out at 775° C. Relative total productivity for the process was found to be 280 hr$^{-1}$. Catalyst productivity as a function of time on stream is plotted in the Figure. It was found that this was the most productive process even though the process was carried out at only 775° C., which was lower than the temperature employed in the other processes in the comparison study.

The experimental results were also evaluated to determine the maximum selectivity for coupled products and the maximum conversion obtained in each process. A summary of the results is provided in Table 1.

TABLE 1

| Comparison of Process and Catalyst Performance | | | |
|---|---|---|---|
| Catalyst | Reaction Temperature °C. | Maximum Selectivity % | Maximum Conversion % |
| PbO/$SiO_2$ (Prior Art) | 800 | 50 | 16 |
| $PbZrO_3$ | 850 | 58 | 20 |
| $Na_{0.1}PbZrO_3$ | 850 | 70 | 18 |
| $NaPbZrO_3$ | 775 | 78 | 20 |

The data in Table 1 show the methane coupling reactions carried out according to the invention provide significantly higher selectivities and conversions than a similar prior art process carried out with a PbO/$SiO_2$ catalyst. The data also show that combining lead zirconate with Na as a promoter provides a catalyst with improved selectivity for coupled products when compared with PbZrO₃. Use of the lead zirconate catalyst containing the promoter also provides an improvement in maximum conversion when compared with the prior art process.

Instantaneous productivity as a function of time on stream provides an indication of the relative catalyst life for each catalyst tested. A catalyst with a high instantaneous productivity has a longer life than a catalyst with a lower instantaneous productivity. The Figure shows that all of the lead zirconate catalysts had a longer catalyst life in the regenerative process mode than the PbO/SiO₂ catalyst of the prior art. The Figure also shows that the catalysts of the invention had a longer life than PbZrO₃. This is an advantage because reactor productivity is increased by extending catalyst life.

Taken together, the Figure and Table 1 show that the catalyst of the invention has a much greater activity at comparable time-on-stream than a conventional supported PbO catalyst. In addition, the catalyst of the invention has much greater selectivity for higher order hydrocarbons. As previously noted, the catalyst of the invention can be maintained at a higher temperature than the PbO catalyst because PbO melts and volatilizes at 888° C. Finally, the catalyst of the invention has longer catalyst life.

The higher order hydrocarbons produced by the invention can be easily transported. They have versatile applications in chemical processing as well as uses as fuels. The higher order hydrocarbons can be further processed to form substantially liquid hydrocarbon products. For example, ethane can be converted to LPG and gasoline and/or an aromatics concentrate as described in United States patent 4,100,218 to Chen et al. The ethane can be subjected to thermal cracking at temperatures of from about 815° C. to about 875° C. to produce an olefin-rich effluent, which can be cooled to a temperature between about 315° C. and about 650° C. and contacted with a crystalline aluminosilicate zeolite to produce a liquid hydrocarbon product suitable for use as LPG, gasoline and/or the aromatics concentrate.

The process of the invention for upgrading low molecular weight alkanes to higher order hydrocarbon products can be integrated into a further process for converting the products to useful chemicals. For example, processes are available for the conversion of ethane and ethylene to ethanol, ethylene glycol, polyethylene and other chemicals useful as fuels, fuel additives and lubricants.

This invention will be more fully understood by reference to the following examples. It is to be understood that these examples are utilized for illustrative purposes only, and are not intended in any way to be limitative of the invention.

EXAMPLES

Catalysts were prepared as described below. Some of the catalysts were then used in a process to convert low molecular weight alkanes to higher molecular weight hydrocarbons. Reaction products were measured to determine individual yields and conversion rates.

EXAMPLE 1

A. Catalyst Preparation—Preparation of NaPbZrO₃

A lead zirconate catalyst containing sodium as a catalyst promoter had the formula

wherein
 B is Na;
 z=1
 a=0
 b=1
 x=3.

The catalyst was substantially free of PbO and uncombined Pb and was prepared as follows.

Water (100 cc) was added to a vessel provided with a mechanical stirrer and the water was heated to a temperature of about 90° C. Lead nitrate ((Pb(NO₃)₂; 50g)) and sodium nitrate (NaNO₃; 13g) were dissolved in the hot water with stirring to form a solution. A zirconia sol (20% ZrO₂; 92g) was impregnated with Pb and Na by adding the zirconia sol to the solution and stirring the resulting mixture until dry.

The zirconia impregnated with Pb and Na was dried for two days at 120° C. The resulting dried product was calcined in two stages. In the first stage, the product was heated at a temperature of 290° C. for 3 hours. The product was subsequently heated at 425° C. for an additional 3 hours in the second stage.

The calcined zirconia impregnated with Pb and Na was ground by mortar and pestle and subsequently sieved. The portion within 20 to 35 mesh was recovered and then calcined at 800° C. for 3 hours to form 25 g of unsupported NaPbZrO₃ catalyst. The surface area of the catalyst was measured by B.E.T. nitrogen adsorption and was found to be 0.40 m²/g.

B. Methane Coupling with NaPbZrO₃ (Cyclic Process)

This example demonstrates the upgrading of methane utilizing the catalyst prepared in Example 1A in a cyclic process, that is, a process cycling between a reaction step and a catalyst re-oxidation step.

The oxidation of methane was performed using a commercial grade of methane comprising about 99.7 percent methane and about 0.3 percent ethane as a feed stream. Methane was passed through a quartz tube in an electrically heated furnace. The catalyst material was placed in the tube near the center of the heated zone of the furnace in a bed less than 50 mm long. The remaining heated portion of the tube was filled with fused quartz chips to provide a preheated initial zone and to decrease residence time after the catalyst. A thermocouple extended into the top few millimeters of the catalyst bed to allow direct temperature measurements.

The catalyst was heat-treated in the reactor prior to methane conversion. An oxygen/nitrogen gas was passed over the heated catalyst at about 150 cc/minute. Temperature rise was gradual, heating from room temperature to about 775° C. over a period of about 2 hours. The final temperature, about 775° C., was maintained for about 1 hour prior to the introduction of the methane portion of the feed into the reactor.

Pulses of methane gas (0.5 cc/pulse) were fed to the reactor over a period of 1.3 sec/pulse. After passing each methane pulse through the reactor, ethylene, ethane and methane were separated on a 10' long Porapak QS column in a VARIAN 3300 Gas Chromatograph with flame ionization detector. Relative molar responses according to Dietz were used to obtain the ratio of hydrocarbon products to methane from the flame detector area. These are close to the unit response per carbon atom rule which applies to flame ionization of hydrocarbons. Oxygen, nitrogen, methane, carbon dioxide and carbon monoxide were determined with a Fisher 1200 Gas Chromatograph where the lighter gases were separated on molecular sieve 13X in parallel with a column for separating carbon dioxide and heavier hydrocarbons, especially $C_3$ and $C_4$ hydrocarbons.

A total of 85 ml of methane was passed over about 0.2 cc of the catalyst in 169 equal methane pulses at 775° C. Table 2 summarizes the results obtained after the indicated number of methane pulses. Table 2 includes the percent conversion after the indicated methane pulse and the percent selectivity to coupled products and by-products CO and $CO_2$.

TABLE 2

Methane Conversion and Product Selectivity in Cyclic Process Using $NaPbZrO_3$ Catalyst

| Methane Pulse No. | Conversion % | Selectivity % | | | | | |
|---|---|---|---|---|---|---|---|
| | | $C_2H_4$ | $C_2H_6$ | $C_3H_6$ | $C_3H_8$ | CO | $CO_2$ |
| 1 | 20 | 12 | 38 | 0.9 | 1.7 | 0 | 48 |
| 6 | 13 | 16 | 60 | 1.1 | 2.2 | 0 | 20 |
| 13 | 12.3 | 14.6 | 63 | Tr | 1.9 | 0 | 19.5 |
| 24 | 9.65 | 13 | 70 | — | 2 | 0 | 14.5 |
| 36 | 8.7 | 12.6 | 70 | Tr | Tr | 0 | 15 |
| 47 | 5.8 | 11 | 69 | Tr | Tr | 0 | 19 |
| 58 | 4.2 | 9.5 | 64 | 0 | 0 | 0 | 26 |
| 69 | 4 | 0 | 66 | 0 | 0 | 0 | 25 |
| 169 | 6.4 | 10 | 70 | Tr | Tr | 0 | 19 |

Table 2 shows that the process of the invention can be carried out at commmercially acceptable methane conversions and selectivities to higher order hydrocarbons in a cyclic mode. The formation of $C_2$ hydrocarbons predominated when the process was carried out at 775° C.

At the completion of the experiment, catalyst reoxidation was carried out by feeding gaseous oxygen to the reactor at 150 cc/min for 30 min at 775° C. Methane was then pulsed over the catalyst as described above and results similar to the first experiment were obtained.

EXAMPLE 2

A. Catalyst Preparation—Preparation of $PbZrO_3$ on $SiO_2$ (50/50)

A lead zirconate catalyst on a silica support had the formula $$Pb\ Zr_z\ A_a\ B_b\ O_x$$

wherein
z=1
a=0
b=0
x=3.

The catalyst was substantially free of PbO and uncombined Pb and was prepared as follows.

Water (75 cc) was added to a vessel provided with a mechanical stirrer and the water was heated to a temperature of about 90° C. Lead nitrate (($Pb(NO_3)_2$; 13.25 g) was dissolved in the hot water with stirring to form a solution. A zirconia sol (20% $ZrO_2$; 24.6 g) was impregnated with Pb by adding the zirconia sol to the solution and stirring the resulting mixture. A silica sol (40% $SiO_2$; 34.6 g) was then added to the mixture and the mixture was stirred until dry.

The zirconia impregnated with Pb on $SiO_2$ was dried at 120° C. overnight. The resulting dried product was calcined in two stages. In the first stage, the product was heated at a temperature of 290° C. for 3 hours. The product was subsequently heated at 425° C. for an additional 3 hours in the second stage.

The calcined zirconia impregnated with Pb was ground by mortar and pestle and subsequently sieved. The portion within 25 to 35 mesh was recovered and then calcined at 800° C. for 2 hours to form 20 g of $PbZrO_3$ catalyst on $SiO_2$ as catalyst support. The supported catalyst contained 50% by weight $PbZrO_3$ and 50% by weight $SiO_2$. The surface area of the catalyst was measured by B.E.T. nitrogen adsorption and was found to be 70 m$^2$/g.

B. Methane Coupling with $PbZrO_3$ on Silica (Cofed Oxygen)

The $PbZrO_3$ on silica catalyst (1.5 cc; 1.5 g) prepared in Example 2A was loaded into a quartz tube reactor having a 7 mm I.D. The catalyst was held in place in the tube with quartz chips. The quartz tube was placed in an electrically heated furnace and a thermocouple was placed in a central 3 mm I.D. thermocouple well to allow direct temperature measurements.

A gas mixture containing methane/oxygen/nitrogen was passed through the catalyst bed. The methane was a commercial grade containing about 99.7 volume percent methane and about 0.3 volume percent ethane.

The catalyst temperature and the relative proportions of methane, oxygen and nitrogen in the gas mixture were varied. The flow rate of the gas mixture was also varied to provide contact times of about 0.1 to 0.4 sec. with the catalyst. The contact time of the gas mixture with coarse quartz chips following the catalyst bed was less than 1 sec.

After passing the gas mixture through the reactor, the higher order hydrocarbons produced were separated and measured as described in Example 1B. The conversion of methane to the higher order hydrocarbons and the selectivity for $C_2$ and other higher hydrocarbons were calculated. The results are summarized in Table 3.

TABLE 3

Methane Conversion and Product Selectivity Using $PbZrO_3$ on $SiO_2$ With Cofed $O_2$ With Varying Reaction Temperatures, Methane Flow Rates and Reactant Gas Compositions

| Exp. No. | $CH_4/O_2/N_2$ | Cat. Temp. | $CH_4$ (g $CH_4$/g cat.-hr) | Per Pass Conversion to: | | | | | $C_{2+}$ Selectivity % | $C_2$ Olefin/ Saturate |
|---|---|---|---|---|---|---|---|---|---|---|
| | | | | $C_2H_6*$ % | $C_2H_4$ % | $C_3$ % | $C_4$ % | Total % | | |
| 1 | 1/.114/.26 | 786° C. | 1.3 | 0.17 | 0.35 | — | — | 0.5 | 77.1 | 0.28 |
| 2 | 1/.046/.24 | 928° C. | 4.6 | 0.68 | 1.62 | 0.10 | 0.01 | 2.4 | 83.1 | 0.90 |
| 3 | 1/.112/.27 | 931° C. | 4.0 | 1.02 | 2.19 | 0.17 | 0.02 | 3.4 | 73.3 | 1.02 |
| 4 | 1/.114/.26 | 879° C. | 1.4 | 0.83 | 2.18 | 0.19 | 0.04 | 3.2 | 63.8 | 1.12 |
| 5 | 1/.114/.26 | 930° C. | 1.5 | 0.60 | 5.09 | 0.72 | 0.31 | 6.7 | 62.0 | 2.99 |
| 6 | 1/.151/.26 | 930° C. | 1.4 | 0.64 | 5.47 | 0.75 | 0.27 | 7.1 | 51.7 | 3.12 |

TABLE 3-continued

Methane Conversion and Product Selectivity Using $PbZrO_3$ on $SiO_2$
With Cofed $O_2$ With Varying Reaction Temperatures, Methane Flow Rates and Reactant Gas Compositions

| Exp. No. | $CH_4/O_2/N_2$ | Cat. Temp. | $CH_4$ (g $CH_4$/g cat.-hr) | Per Pass Conversion to: | | | | | $C_{2+}$ Selectivity % | $C_2$ Olefin/ Saturate |
|---|---|---|---|---|---|---|---|---|---|---|
| | | | | $C_2H_6$* % | $C_2H_4$ % | $C_3$ % | $C_4$ % | Total % | | |
| 7 | 1/.151/.26 | 956° C. | 1.4 | 0.01 | 6.77 | 1.31 | 0.34 | 8.4 | 54.6 | 6.05 |

*Ethane, equivalent to 1.1% methane conversion, present in both feed and product streams was assumed unconverted and not included in this yield.

Experiment No. 1 in Table 3 shows that when the process is carried out with cofed oxygen, the total conversion of methane to higher order hydrocarbons was only 0.5% when the $PbZrO_3/SiO_2$ catalyst was heated at the relatively low temperature of 786° C. The reaction products were comprised only of $C_2$ higher order hydrocarbons.

A comparison of Experiment No. 1 with Experiment No. 3 in Table 3 shows that the total conversion percentage can be substantially increased from 0.5% to 3.4% by increasing the catalyst temperature from 786° C. to 931° C., which is above the temperature of 888° C. at which PbO (litharge) volatilizes. Since the catalyst was substantially free of PbO and uncombined Pb, the process could be operated at the higher temperature without risk to the environment or risk of lead volatilization.

Increasing the catalyst temperature also resulted in an increase of more than three-fold in the $C_2$ olefin/saturate ratio from 0.28 to 1.02. A hydrocarbon product mixture rich in olefins is advantageous because olefins are more readily converted by thermal and catalytic methods to easily transportable liquid hydrocarbons than are saturated hydrocarbons. In addition, olefins generally have greater commercial value.

When Experiment No. 1 is compared with Experiment No. 2 in Table 3, it is seen that a higher methane conversion percentage is obtained when the catalyst temperature is increased from 786° C. to 928° C. even though the amount of 02 in the reaction gas mixture is decreased. Table 3 also shows that these conditions resulted in high selectivity for higher order ($C_{2+}$) hydrocarbons.

Reactor productivity can be increased by operating at a higher catalyst temperature. This is evident from a comparison of Experiment Nos. 2 and 3 with Experiment No. 1, wherein the space velocity of the reaction gas mixture (g $CH_4$/g cat.-hr) was higher in Experiment Nos. 2 and 3 than in Experiment No. 1.

Increasing catalyst temperature without a substantial change in the space velocity of the reaction gas mixture gives a substantially higher total conversion to higher order hydrocarbons and a higher $C_2$-olefin/saturate ratio with a modest reduction in selectivity. This is shown in Experiment Nos. 4 and 5 in Table 3.

Increasing the oxygen content in the reaction gas mixture while heating the catalyst at high temperatures and feeding the mixture to the reactor at low space velocities gives especially high yields of $C_2$-olefin, $C_3$ and $C_4$ hydrocarbons. Selectivity is still over 50% under these conditions. This is shown by comparing Experiment No. 6 with Experiment No. 5 in Table 3. A further comparison of Experiment No. 5 with Experiment No. 7 shows that an additional increase in catalyst temperature produces even more $C_2$ olefin, $C_3$ and $C_4$ hydrocarbons with very little $C_2H_6$ over that in the feed.

EXAMPLE 3

A. Catalyst Preparation—Preparation of $PbZr_{15}Y_{0.8}Na_{0.5}O_x$

A lead zirconate catalyst had the formula

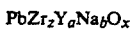

wherein
z=15
a=0.8
b=0.5.

The catalyst was substantially free of PbO and was prepared as follows.

A yttrium stabilized zirconia (18.48 g; 5 weight percent Y) was placed in a round bottomed flask. While maintaining a partial vacuum of approximately 50 mm Hg and a temperature of 50° C., a solution containing 3.312 g of lead nitrate and 0.42 g of sodium nitrate in 50 ml of warm (50° C.) water was allowed to slowly drip onto the Y stabilized zirconia. During this process, the round bottomed flask was allowed to slowly rotate to assure even distribution of the aqueous solution. This process required two and one half hours.

The catalyst was heat-treated in four stages as follows. In the first stage, the catalyst was heated at 120° C. for 16 hours. The catalyst was heated at 295° C. for 3 hours in the second stage and at 425° C. for 3 hours in the third stage. A final heat-treatment stage was carried out at 825° C. for 24 hours.

Analysis of the resulting catalyst indicated that the catalyst was substantially free of PbO and uncombined Pb. The catalyst had a surface area of 1.8 m²/g as measured by B.E.T. nitrogen adsorption.

B. Methane Coupling with $PbZr_{15}Y_{0.8}Na_{0.5}O_x$ (Cofed Oxygen)

The catalyst (0.6 cc; 0.85 g) prepared in Example 3A was used in a methane coupling reaction in the manner described in Example 2B, except that analysis was accomplished by means of an on-line Questor mass spectrometer. Internal catalyst temperatures were not measured, but the temperatures were higher than the reported set-point temperatures. The feed stream to the reactor was comprised of methane/oxygen/argon, wherein the methane consisted of 99.7 volume percent methane and 0.3 volume percent ethane.

The conversion of methane to higher order hydrocarbons and the selectivity for $C_2$ and other higher hydrocarbons were calculated. The results are summarized in Table 4.

TABLE 4

Methane Conversion and Product Selectivity Using $PbZr_{15}Y_{0.8}Na_{0.5}O_x$
With Cofed $O_2$ With Varying Reaction Temperatures,
Constant Flow Rate and Varying Reactant Gas Compositions

| Exp. No. | $CH_4/O_2/Ar$ | Cat. Set-Point | GHSV $hr^{-1}$ | Per Pass Conversion To: $C_2H_6$ % | $C_2H_4$ % | Total % | $C_{2+}$ selectivity % | $C_2$ Olefin/ Saturate |
|---|---|---|---|---|---|---|---|---|
| 1 | 1/.11/.30 | 750° C. | 15540 | 2.5 | 3.4 | 5.9 | 60 | 1.4 |
| 2 | 1/.05/.30 | 750° C. | 15540 | 2.2 | 2.4 | 4.6 | 63 | 1.1 |
| 3 | 1/.11/.30 | 800° C. | 15540 | 1.6 | 5.8 | 5.8 | 53 | 2.6 |
| 4 | 1/.05/.30 | 800° C. | 15540 | 1.4 | 2.8 | 4.2 | 54 | 2 |
| 5 | 1/.11/.30 | 850° C. | 15540 | 0.5 | 4.6 | 5.1 | 41 | 9.2 |
| 6 | 1/.05/.30 | 850° C. | 15540 | 0.4 | 3.4 | 3.8 | 51 | 8.5 |

Reference to Table 4 shows that conversion could be carried out at a temperature as high as 850° C., and since the catalyst is substantially free of PbO and uncombined Pb, there was no risk of volatilization of the lead component of the catalyst. The data in Table 4 also shows that the proportion of the more valuable unsaturated hydrocarbons in the product can be increased by increasing the catalyst set-point temperature. Moreover, it will be appreciated from the data in Table 4 that the experiments were carried out at a relatively high GHSV compared to prior art processes that are typically carried out at a GHSV of about 800 $hr^{-1}$. When the process was carried out at a higher temperature (950° C.), the concentration of CO in the product stream increased. Since the product recovery and analysis apparatus were not selective for other valuable products, such as methanol, it was not possible to determine whether the carbon monoxide in the product stream was formed by direct conversion of methane or from the decomposition of methanol.

In summary, this invention provides a Pb-containing catalyst that is substantially free of PbO and uncombined lead. The catalyst is suitable for upgrading a low molecular weight alkane to a higher order hydrocarbon even at a high reaction temperature. The invention also provides a process for using the catalyst. The catalyst exhibits high activity in converting alkanes to higher order hydrocarbons, including liquid hydrocarbon products. The catalyst is very stable at high temperatures; it does not volatilize. The catalyst retains its chemical activity, structural integrity and mechanical properties at temperatures up to about 1550° C. Volatilization of Pb or PbO from the catalyst is negligible at temperatures up to about 1550° C. The catalyst has long catalyst life. It is suitable for use in natural gas conversion to higher order hydrocarbon products at high selectivities. Since the catalyst is effective in coupling methane at high reactant feed rates, the process of the invention can be carried out at commercially feasible methane conversion rates. The catalyst of the invention is not known to form stable carbonates with $CO_2$ in the product stream, which could otherwise adversely affect catalyst life and reactor productivity. The process of the invention is especially useful for upgrading methane to produce predominantly ethane and ethylene.

We claim:

1. A catalyst for the conversion of a low molecular weight alkane to a higher order hydrocarbon, wherein said catalyst comprises a composition having the formula $$Pb\ Zr_z\ A_a\ B_b\ O_x$$

wherein
A is Mg, Ca, Sr, Ba, Zn, Ce, Sc, Y, Ti, Hf, or mixtures thereof;
B is Li, Na, K, Rb, Cs or mixtures thereof; and
wherein
z is about 1 to about 100;
a is 0.0 to about 100;
b is about 0.1 to about 100;
x is the number of oxygens needed to fulfill the valence requirements of the other elements; and
wherein (a+b) is about 0.1 to about 100, and the catalyst is substantially free of PbO and uncombined Pb.

2. Catalyst in accordance with claim 1, wherein A is selected from the group consisting of Mg, Ca, Y, Ti and mixtures thereof.

3. Catalyst in accordance with claim 1, wherein A is selected from the group consisting of Mg, Ca or mixtures thereof.

4. Catalyst in accordance with claim 1, wherein B is selected from the group consisting of Li, Na, K and mixtures thereof.

5. Catalyst in accordance with claim 1, wherein B is Na.

6. Catalyst in accordance with claim 1, wherein the value of a is 0.

7. Catalyst in accordance with claim 1, wherein the value of b is about 0.5 to about 1.

8. Catalyst in accordance with claim 1, wherein the value z is about 1 to about 15.

9. Catalyst in accordance with claim 1, wherein said catalyst is supported on a carrier.

10. Catalyst in accordance with claim 1, wherein said carrier is selected from the group consisting of alumina, silica, alumina silica, silicon carbide and clay.

11. A catalyst for the conversion of a low molecular weight alkane to a higher order hydrocarbon, wherein said catalyst consists essentially of a composition having the formula $$Pb\ Zr_z\ A_a\ B_b\ O_x$$

wherein
A is Mg, Ca, Ti or mixtures thereof;
B is Li, Na, K or mixtures thereof; and wherein
z is about 1 to about 100;
a is 0.0 to about 3;
b is about 0.1 to about 3;
x is the number of oxygens needed to fulfill the valence requirements of the other elements; and
wherein (a+b) is about 0.1 to about 3, and the catalyst is substantially free of Pbo and uncombined Pb.

12. Catalyst in accordance with claim 11, wherein B is Na.

13. Catalyst in accordance with claim 12, wherein the value of a is 0.

14. Catalyst in accordance with claim 13, wherein the value of b is about 0.5 to about 1.

15. Catalyst in accordance with claim 14, wherein the value of z is about 1 to about 15.

16. Catalyst in accordance with claim 15, wherein said catalyst is supported on a carrier.

17. Catalyst in accordance with claim 11, wherein (a+b) is about 0.1 to about 2.

18. Catalyst in accordance with claim 11, wherein (a+b) is equal to the value of x.

19. A catalyst for the conversion of a low molecular weight alkane to a higher order hydrocarbon, wherein said catalyst comprises a composition having the formula $$Pb\ Zr_z\ A_a\ B_b\ O_x$$

wherein
A is Mg, Ca, Sr, Ba, Zn, Ce, Sc, Y, Ti, Hf, or mixtures thereof;
B is Li, Na, K, Rb, Cs or mixtures thereof; and wherein
z is about 1 to about 100;
a is 0.0 to about 100;
b is 0.0 to about 100;
x is the number of oxygens needed to fulfill the valence requirements of the other elements; and
wherein (a+b) is about 0.1 to about 100, the catalyst is substantially free of PbO and uncombined Pb, and the catalyst is supported on a carrier.

20. A catalyst in accordance with claim 9, wherein said carrier is selected from the group consisting of alumina, silica, alumina-silica, silicon carbide and clay.

21. A catalyst for the conversion of a low molecular weight alkane to a higher order hydrocarbon, wherein said catalyst consists essentially of a composition having the formula $$Pb\ Zr_z\ A_a\ B_b\ O_x$$

wherein
A is Mg, Ca, Ti or mixtures thereof;
B is Li, Na, K or mixtures thereof; and wherein
z is about 1 to about 100;
a is 0.0 to about 3;
b is 0.0 to about 3;
x is the number of oxygens needed to fulfill the valence requirements of the other elements; and
wherein (a+b) is about 0.1 to about 3, the catalyst is substantially free of PbO and uncombined Pb, and the catalyst is supported on a carrier.

* * * * *